(12) United States Patent
Kondo et al.

(10) Patent No.: US 10,183,083 B2
(45) Date of Patent: Jan. 22, 2019

(54) METAL MESH, STERILIZATION DETERMINATION METHOD, AND CLEANING DETERMINATION METHOD

(71) Applicant: Murata Manufacturing Co., Ltd., Nagaokakyo-shi, Kyoto-fu (JP)

(72) Inventors: Takashi Kondo, Nagaokakyo (JP); Wataru Yamamoto, Nagaokakyo (JP)

(73) Assignee: MURATA MANUFACTURING CO., LTD., Nagaokakyo-shi, Kyoto-Fu (JP)

( * ) Notice: Subject to any disclaimer, the term of this patent is extended or adjusted under 35 U.S.C. 154(b) by 155 days.

(21) Appl. No.: 15/454,028

(22) Filed: Mar. 9, 2017

(65) Prior Publication Data

US 2017/0173194 A1    Jun. 22, 2017

Related U.S. Application Data

(63) Continuation of application No. PCT/JP2016/072788, filed on Aug. 3, 2016.

(30) Foreign Application Priority Data

Aug. 7, 2015 (JP) .................................. 2015-156775

(51) Int. Cl.

| | |
|---|---|
| *A61L 2/08* | (2006.01) |
| *A61L 2/28* | (2006.01) |
| *G01N 31/22* | (2006.01) |
| *B08B 3/08* | (2006.01) |
| *B01D 35/143* | (2006.01) |
| *B01D 39/10* | (2006.01) |

(Continued)

(52) U.S. Cl.
CPC ................. *A61L 2/081* (2013.01); *A61L 2/08* (2013.01); *A61L 2/28* (2013.01); *B01D 35/143* (2013.01);

(Continued)

(58) Field of Classification Search
CPC ... A61L 2/08; A61L 2/081; A61L 2/28; B01D 35/143; B01D 39/10; B07B 1/4609;

(Continued)

(56) References Cited

U.S. PATENT DOCUMENTS

| | | | |
|---|---|---|---|
| 6,413,689 B1 * | 7/2002 | Hori | ......................... G03G 5/04 430/127 |
| 6,730,113 B2 | 5/2004 | Eckhardt et al. | |

(Continued)

FOREIGN PATENT DOCUMENTS

| | | |
|---|---|---|
| JP | S48-037433 Y1 | 11/1973 |
| JP | H05-043827 A | 2/1993 |

(Continued)

OTHER PUBLICATIONS

International Search Report issued in International Application No. PCT/JP2016/072788, dated Oct. 11, 2016.

(Continued)

*Primary Examiner* — Jennifer Wecker

(74) *Attorney, Agent, or Firm* — Arent Fox LLP

(57) ABSTRACT

A metal mesh has a plurality of through-holes. A photosensitive organic material is attached to at least part of the metal mesh. The metal mesh is sterilized and/or cleaned. A determination of whether or not the sterilization and/or cleaning has been successful is made by analyzing the photosensitive organic material attached to the metal mesh.

15 Claims, 6 Drawing Sheets

(51) Int. Cl.
  *B07B 1/46* (2006.01)
  *B07B 1/50* (2006.01)
  *B08B 3/00* (2006.01)
  *B08B 13/00* (2006.01)
  *B08B 3/12* (2006.01)

(52) U.S. Cl.
  CPC ............ *B01D 39/10* (2013.01); *B07B 1/4609* (2013.01); *B07B 1/50* (2013.01); *B08B 3/00* (2013.01); *B08B 3/08* (2013.01); *B08B 13/00* (2013.01); *G01N 31/226* (2013.01); *B08B 3/12* (2013.01)

(58) Field of Classification Search
  CPC .. B07B 1/50; B08B 13/00; B08B 3/00; B08B 3/08; B08B 3/12; G01N 31/226
  See application file for complete search history.

(56) References Cited

U.S. PATENT DOCUMENTS

| | | |
|---|---|---|
| 2003/0017073 A1 | 1/2003 | Eckhardt et al. |
| 2003/0018373 A1 | 1/2003 | Eckhardt et al. |
| 2003/0031586 A1 | 2/2003 | Eckhardt et al. |
| 2004/0034398 A1 | 2/2004 | Eckhardt et al. |
| 2014/0238863 A1* | 8/2014 | Suzuki .................... C25D 1/08 205/75 |
| 2016/0195458 A1 | 7/2016 | Kikuhara et al. |
| 2017/0128858 A1 | 5/2017 | Suzuki et al. |

FOREIGN PATENT DOCUMENTS

| | | | |
|---|---|---|---|
| JP | 2000-065934 A | | 3/2000 |
| JP | 2005-508664 A | | 4/2005 |
| JP | 2008-055282 A | | 3/2008 |
| JP | 2009-143731 A | | 7/2009 |
| JP | 2014-125652 A | | 7/2014 |
| JP | 2014125652 A | * | 7/2014 |
| WO | WO 2013/054766 A1 | | 4/2013 |
| WO | WO 2015/019889 A1 | | 2/2015 |

OTHER PUBLICATIONS

Written Opinion of the International Searching Authority issued in International Application No. PCT/JP2016/072788, dated Oct. 11, 2016.

* cited by examiner

METAL MESH, STERILIZATION DETERMINATION METHOD, AND CLEANING DETERMINATION METHOD

CROSS REFERENCE TO RELATED APPLICATIONS

The present application is a continuation of International application No. PCT/JP2016/072788, filed on Aug. 3, 2016, which claims priority to Japanese Patent Application No. 2015-156775, filed on Aug. 7, 2015, the entire contents of each of which are incorporated herein by reference.

BACKGROUND OF THE INVENTION

The present invention relates to a metal mesh that allows determination of whether the metal mesh has undergone at least one of sterilization and cleaning, a sterilization determination method for determining whether the metal mesh has been sterilized, and a cleaning determination method for determining whether the metal mesh has been cleaned.

In recent years, cell trapping systems for trapping cells in a fluid have been disclosed (see, for example, International Publication No. 2015/019889). In the cell trapping system disclosed in the foregoing publication, the filter used for trapping cells is sterilized and cleaned before the cells are trapped.

However, in the foregoing cell trapping system the conditions of the filter itself before and after sterilization and cleaning are unlikely to differ, making it difficult to determine whether the filter has been sterilized and cleaned.

An object of the present invention is to provide a metal mesh that allows determination of whether the metal mesh has undergone at least one of sterilization and cleaning, a sterilization determination method for determining whether the metal mesh has been sterilized, and a cleaning determination method for determining whether the metal mesh has been cleaned.

BRIEF DESCRIPTION OF THE INVENTION

A metal mesh in an aspect of the present invention is a metal mesh having plural through-holes. The metal mesh has a photosensitive organic material attached to at least part of the metal mesh.

A sterilization determination method in an aspect of the present invention is a sterilization determination method for determining whether a metal mesh has been sterilized. The sterilization determination method includes attaching a photosensitive organic material to at least part of the metal mesh, sterilizing the metal mesh, and determining whether the metal mesh has been sterilized on the basis of a modification of the photosensitive organic material.

A cleaning determination method in an aspect of the present invention is a cleaning determination method for determining whether a metal mesh has been cleaned. The cleaning determination method includes attaching a photosensitive organic material to at least part of the metal mesh, cleaning the metal mesh, and determining whether the metal mesh has been cleaned on the basis of a change in the amount of the photosensitive organic material attached to the metal mesh.

According to the present invention, there are provided a metal mesh that allows determination of whether the metal mesh has undergone at least one of sterilization and cleaning, a sterilization determination method for determining whether the metal mesh has been sterilized, and a cleaning determination method for determining whether the metal mesh has been cleaned.

A metal mesh in an aspect of the present invention is a metal mesh having a plurality of through-holes. The metal mesh may have a photosensitive organic material attached to at least part of the metal mesh. This configuration makes it easy to determine whether the metal mesh has undergone at least one of sterilization and cleaning.

The photosensitive organic material may be a radiation-sensitive organic material that undergoes a modification by radiation exposure. According to this configuration, the photosensitive organic material that has undergone a modification by radiation exposure makes it easier to determine whether the metal mesh has been sterilized.

The photosensitive organic material may contain carbon. This composition makes it easier to determine whether the metal mesh has been cleaned.

The photosensitive organic material may be attached to at least part of the inner walls of the plurality of through-holes. This configuration makes it possible to efficiently sterilize or clean the metal mesh. This configuration also makes it easy to determine whether the inner walls of the through-holes of the metal mesh, which are difficult to sterilize or clean, have been sterilized or cleaned.

The photosensitive organic material may be attached to only the inner walls of the plural through-holes. This configuration makes it possible to efficiently sterilize or clean the metal mesh. This configuration makes it easy to determine whether the inner walls of the through-holes of the metal mesh, which are difficult to sterilize or clean, have been sterilized or cleaned.

A sterilization determination method in an aspect of the present invention is a sterilization determination method for determining whether a metal mesh has been sterilized. The sterilization determination method may include attaching a photosensitive organic material to at least part of the metal mesh, sterilizing the metal mesh, and determining whether the metal mesh has been sterilized on the basis of a modification of the photosensitive organic material. This method makes it easy to determine whether the metal mesh has been sterilized on the basis of the modification of the photosensitive organic material attached to the metal mesh. This may involve measuring absorbances of the photosensitive organic material both before and after the sterilizing step and determining whether the metal mesh has been sterilized on a basis of the measured absorbances. This process makes it easier to determine whether the metal mesh has been sterilized on the basis of the absorbance of the photosensitive organic material.

The photosensitive organic material may be attached to at least one metal mesh selected from a plurality of metal meshs which are sterilized together. According to this process, whether sterilization has been completed can be determined by attaching the photosensitive organic material to at least one metal mesh selected from plural metal meshs, which enables efficient determination.

A cleaning determination method in an aspect of the present invention is a cleaning determination method for determining whether a metal mesh has been cleaned. The cleaning determination method may include attaching a photosensitive organic material to at least part of the metal mesh, cleaning the metal mesh, and determining whether the metal mesh has been cleaned on the basis of the amount of the photosensitive organic material attached to the metal mesh. This method makes it easy to determine whether the metal mesh has been cleaned on the basis of the amount of the photosensitive organic material attached to the metal mesh.

The determination of whether the metal mesh had been cleaned may involve measuring amounts of carbon in the photosensitive organic material both before and after the cleaning step and determining whether the metal mesh has been cleaned on a basis of the measured amounts of carbon. This process makes it easier to determine whether the metal mesh has been cleaned on the basis of the amount of carbon in the photosensitive organic material.

The photosensitive organic material may be attached on at least one metal mesh selected from a plurality of metal meshs which are cleaned together. According to this process, whether cleaning has been completed can be determined by attaching the photosensitive organic material to at least one metal mesh selected from plural metal meshs, which enables efficient determination.

Embodiments according to the present invention will be described below with reference to the accompanying drawings. In each figure, each element is exaggerated for easy description.

DESCRIPTION OF THE PREFERRED EMBODIMENTS (First Embodiment)
[Overall Structure]

Figure 1:
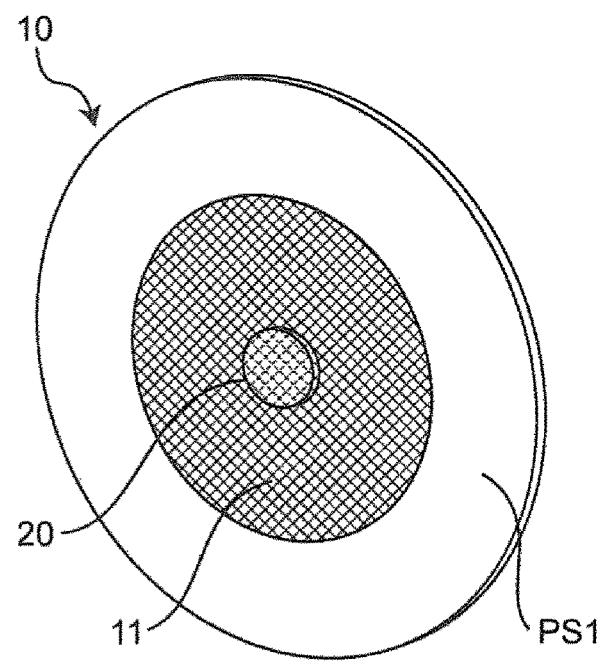
FIG. 1 is a schematic structural view of a metal mesh in a first embodiment according to the present invention.
Figure 2:
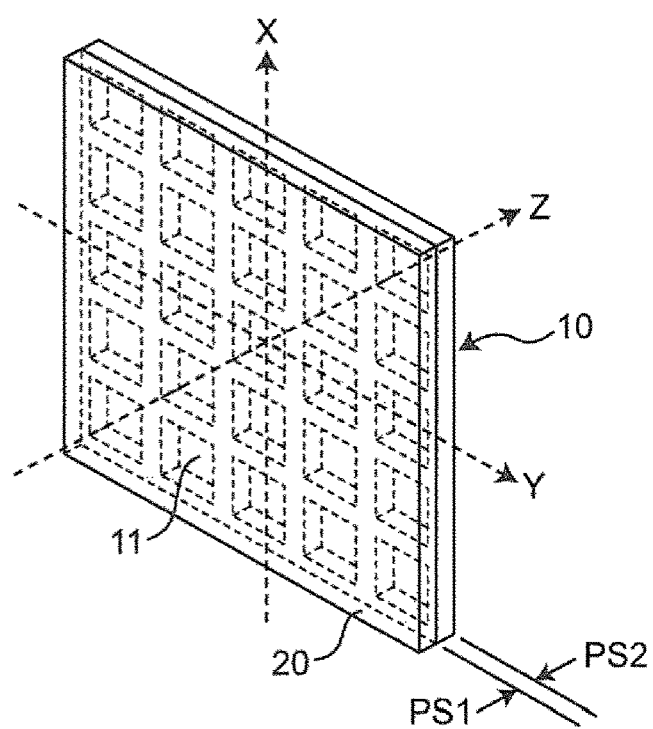
FIG. 2 is an enlarged view of a part of the metal mesh in the first embodiment according to the present invention to which the organic material is attached.

FIG. 1 is a schematic view of a metal mesh 10 in accordance with a first embodiment of the present invention. FIG. 2 is an enlarged view of a part of the metal mesh 10 to which an organic material 20 is attached. The X, Y, and Z directions in FIG. 2 respectively indicate the length direction, the width direction, and the thickness direction of the metal mesh 10. As illustrated in FIG. 1 and FIG. 2, the metal mesh 10 is a metal thin film having a plurality of through-holes 11. The organic material 20 is located on a first principal surface PS1 of the mesh 10 and is used to determine whether sterilization and cleaning have been completed.

The metal mesh 10 separates a filtration object from a fluid containing the filtration object by passing the fluid through the metal mesh 10. The term "filtration object" as used herein refers to an object to be filtered out through the metal mesh 10. Examples of the filtration object include biological materials and PM2.5. The term "biological materials" refers to materials derived from organisms, such as cells (eukaryotes), bacteria (eubacteria), and viruses. Examples of cells (eukaryotes) include ovum, sperm, induced pluripotent stem cells (iPS cells), ES cells, stem cells, mesenchymal stem cells, mononuclear cells, single cells, cell clusters, floating cells, adhesive cells, nerve cells, leucocytes, lymphocytes, cells for regeneration medicine, autologous cells, cancer cells, circulating tumor cells (CTCs), HL-60, HELA, and fungi. Examples of bacteria (eubacteria) include Gram-positive bacteria, Gram-negative bacteria, *Escherichia coli*, and tubercle bacillus. Examples of viruses include DNA viruses, RNA viruses, rotavirus, (bird) influenza viruses, yellow fever virus, dengue virus, encephalitis viruses, hemorrhagic fever viruses, and immunodeficiency viruses. The fluid containing the filtration object may be a liquid or a gas. That is, the metal mesh 10 can be used both when the fluid is a liquid and when the fluid is a gas.

As illustrated in FIG. 1, the metal mesh 10 is a preferably circular metal mesh and as illustrated in FIG. 2, opposing first and second principal surfaces PS1 and PS2 each of which have a plurality of through-holes 11 that penetrate through both of the principal surfaces. The plurality of through-holes 11 are preferably arranged at regular intervals on the first principal surface PS1 and the second principal surface PS2 of the metal mesh 10. The metal mesh 10 is formed of, for example, nickel. The metal mesh 10 is, for example, 6 mm in diameter and 1.2 μm in thickness. The material of the metal mesh 10 may be, for example, gold, silver, copper, nickel, stainless steel, palladium, titanium, or an alloy thereof. In particular, the material of the metal mesh 10 is preferably gold, nickel, stainless steel, and titanium when the metal mesh 10 traps biological materials.

As illustrated in FIG. 2, the metal mesh 10 is a plate-like structure (grid structure) in which the plurality of through-holes 11 are arranged at regular intervals in a matrix manner. The through-holes 11 preferably have a square shape as viewed from the first principal surface PS1 side of the metal mesh 10, that is, as viewed in the Z direction. The through-holes 11 are arranged at the same interval in two array-directions parallel to the sides of the square, that is, in the X direction and the Y direction in FIG. 2. The through-holes 11 do not necessarily have a square shape and may have, for example, a rectangular shape, a circular shape, or an elliptical shape. The array of the through-holes is not limited to a square grid array. The array of the holes may be, for example, a quadrilateral array, such as a rectangular array in which the intervals in two array-directions are not the same, or may be a triangular grid array, a quasi-periodic array, or other arrays.

The through-holes 11 are preferably designed to be 1 μm or more and 50 μm or less in length and 1 μm or more and 50 μm or less in width. The interval between the through-holes 11 is, for example, greater than 1 times the size of the through-holes 11 and equal to or less than 10 times the size of the through-holes 11, and more preferably no more than 3 times the size of the through-holes 11. Alternatively, the opening ratio (i.e., the ratio of the openings to the total surface area of the first principal surface PS1) is preferably 10% or more. The size described above is particularly effective for obtaining an effect of efficiently sterilizing or cleaning the metal mesh 10 and an effect of easily determining whether the inner walls of the through-holes 11, which are difficult to sterilize or clean, have been properly sterilized or cleaned.

The organic material 20 for determining whether sterilization and cleaning have been completed is preferably attached to the first principal surface PS1 of the metal mesh 10. In the first embodiment, the organic material 20 is attached to part of the area having the through-holes 11.

Figure 3:
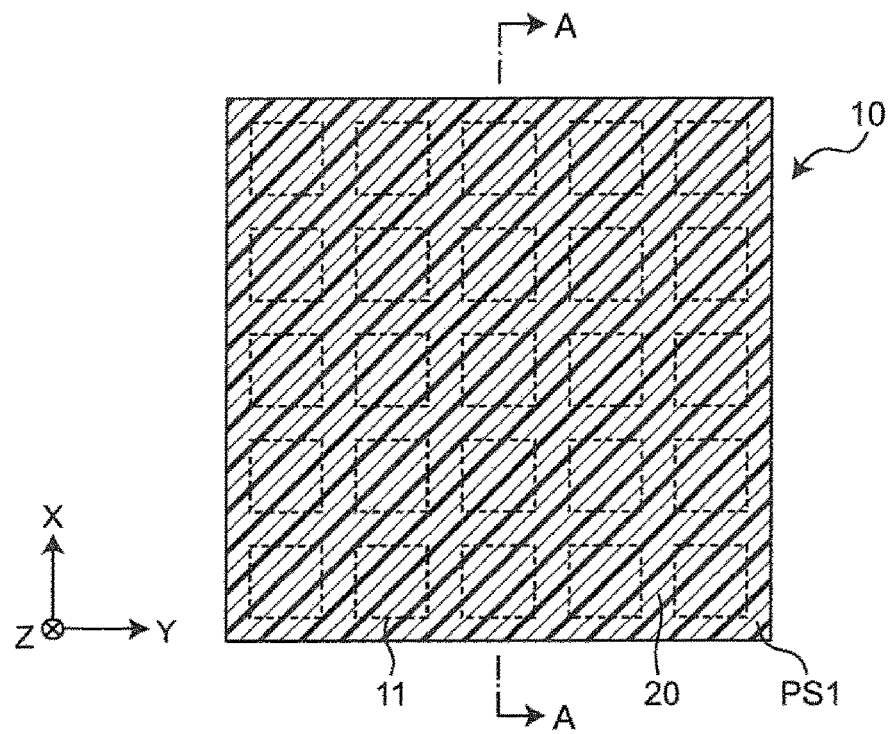
FIG. 3 is a schematic view of the part of the metal mesh of FIG. 2 as viewed from the first principal surface side.
Figure 4:
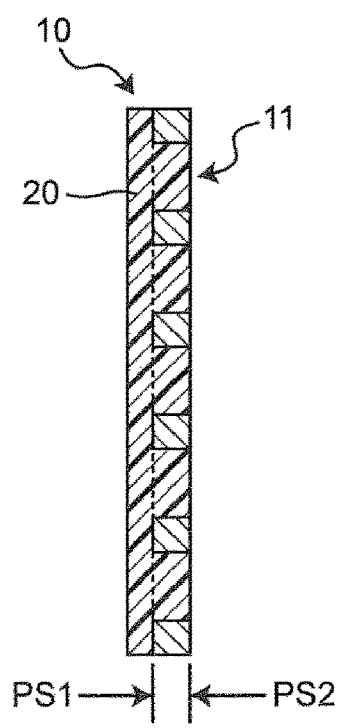
FIG. 4 is a sectional view of a part of the metal mesh of FIG. 3 taken along line A-A.

FIG. 3 is a schematic view of a part of the metal mesh 10 as viewed from the first principal surface PS1 side. FIG. 4 is a sectional view of a part of the metal mesh 10 taken along line A-A. As illustrated in FIG. 3 and FIG. 4, the organic material 20 is attached to the first principal surface PS1 of the metal mesh 10. The organic material 20 is also attached to all or part of the inside of the through-holes 11 of the metal mesh 10.

The organic material 20 is preferably an organic material for determining whether sterilization and cleaning have been completed and is preferably a photosensitive organic material. In this first embodiment, the photosensitive organic material is a radiation-sensitive organic material that undergoes a modification in response to radiation exposure. For example, the photosensitive organic material is an organic material that is composed of a polymer compound and that will produce polymer radicals in response to gamma-ray exposure. When the organic material 20 is subjected to (exposed to) gamma-ray exposure, the organic material 20 is changed in crystallinity, molecular weight, or the like by the breakage or cross-linking of the main chain and the side chains of the polymer compound. In the first embodiment, the term "modification of the organic material 20" refers to, for example, a change in the color of the organic material 20 in response to gamma-ray exposure.

Examples of the organic material 20 include an organic material containing a cyclic rubber and a bisazide compound which serves as a photosensitizer, an organic material containing a novolac resin and a naphthoquinone diazide compound which serves as a photosensitizer (specifically, an organic material containing a novolac resin and a 1,2-naphthoquinone diazide sulfonic acid ester compound which serves as a photosensitizer), polyacetal, polyether imide, polyethylene, polystyrene, polypropylene, and polycarbonate. Examples of the organic material 20 further include an organic material containing a poly(hydroxystyrene)-based resin and a photoacid generator which serves as a photosensitizer, and an organic material containing an acrylic resin and a photoacid generator which serves as a photosensitizer. Examples of the photoacid generator include adamantane and norbornene.

In the first embodiment, the organic material 20 contains carbon in order to determine whether cleaning has been completed.

[Sterilization Determination Method]

Figure 5:
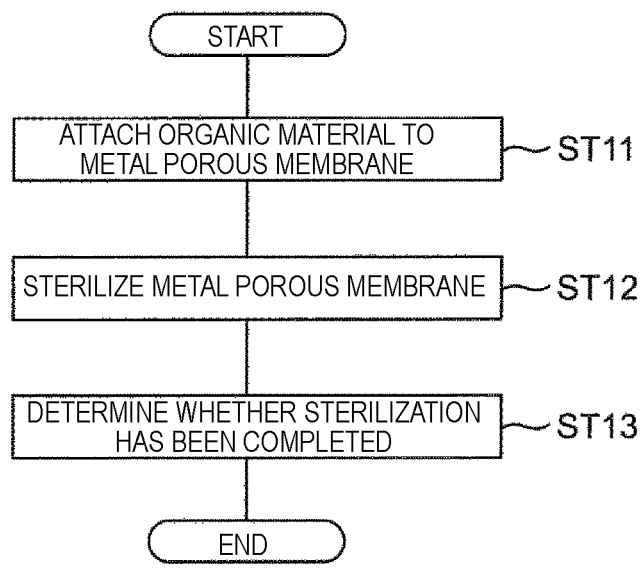
FIG. 5 is a flowchart of a sterilization determination method in the first embodiment according to the present invention.

A sterilization determination method according to the first embodiment of the present invention will be described with reference to FIG. 5. FIG. 5 is a flowchart of the sterilization determination method according to the first embodiment.

As illustrated in FIG. 5, in Step ST11, an organic material 20 for determining whether sterilization has been completed is attached to a surface of a metal mesh 10. Specifically, the organic material 20 is attached to part of the area having through-holes 11 on a first principal surface PS1 of the metal mesh 10. The organic material 20 is also attached to the inside of the through-holes 11 of the metal mesh 10.

In Step ST12, the metal mesh 10 is sterilized. Specifically, the metal mesh 10 having the organic material 20 is sterilized by exposing the metal mesh 10 to gamma rays.

In Step ST13, whether the metal mesh 10 has been sterilized is determined. In the first embodiment, whether the metal mesh 10 has been sterilized is determined on the basis of a change in the color of the organic material 20 before and after the sterilizing step. In Step ST13, whether the metal mesh 10 has been sterilized is determined by measuring the absorbance of the organic material 20 before and after the sterilizing step. The determination of whether the metal mesh 10 has been sterilized on the basis of the absorbance will be specifically described below.

Examples of the method for determining whether sterilization has been completed include the absorbance measurement from the infrared region to the ultraviolet region. Specifically, the absorbance of the organic material before sterilization and after sterilization is measured, and whether sterilization has been completed can be determined on the basis of a spectral change before and after sterilization or on the basis of a color change attributed to a spectral change. Alternatively, as a method for determining whether sterilization has been completed, for example, reculture typified by bacterial culture in an agar medium or Gram staining may be used.

The absorbance measurement may be performed on the inside of the through-holes 11 of the metal mesh 10, which is an area that is relatively difficult to sterilize. When the absorbance measurement on the inside of the through-holes shows that the area that is difficult to sterilize has been sterilized, it can be determined that other areas have also been sterilized. For example, when the absorbance measurement shows that the inside of the through-holes 11 of the metal mesh 10 has been sterilized, it can be determined that the entire metal mesh 10 has been sterilized.

[Cleaning Determination Method]

Figure 6:
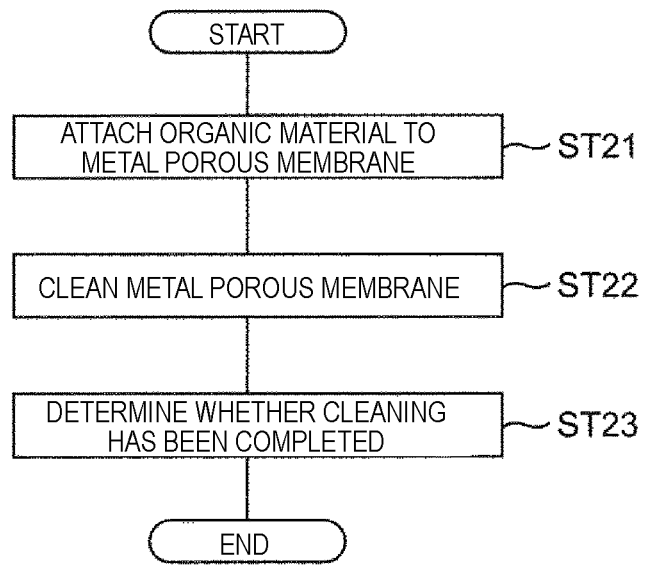
FIG. 6 is a flowchart of a cleaning determination method in the first embodiment according to the present invention.

A cleaning determination method according to the first embodiment of the present invention will be described with reference to FIG. 6. FIG. 6 is a flowchart of the cleaning determination method according to the first embodiment.

As illustrated in FIG. 6, in Step ST21, an organic material 20 for determining whether cleaning has been completed is attached to a surface of a metal mesh 10. Specifically, the organic material 20 is attached to at least part of the area having through-holes 11 on a first principal surface PS1 of the metal mesh 10. The organic material 20 is also attached to the inside of the through-holes 11 of the metal mesh 10.

In Step ST22, the metal mesh 10 is cleaned. Specifically, the metal mesh 10 having the organic material 20 is cleaned with a liquid such as acetone or pure water.

In Step ST23, whether the metal mesh 10 has been cleaned is determined. In the first embodiment, whether the metal mesh 10 has been cleaned is determined by measuring the amount of carbon in the organic material 20 before and after the cleaning step. The determination of whether the metal mesh 10 has been cleaned on the basis of the measurement of the amount of carbon will be specifically described below.

Examples of the method for determining whether cleaning has been completed on the basis of the measurement of the amount of carbon include XPS (X-ray Photoelectron Spectroscopy) measurement. Table 1 shows the results of the XPS analysis after completion of cleaning and before completion of cleaning. The XPS analysis was carried out using an XPS measurement apparatus (Model Quantum 2000 available from ULVAC-PHI, Incorporated). The X-ray beam diameter used in the XPS measurement was 9 μm. The X-ray beam was directed to the inside (inner walls) of the holes 11 in a central portion of the metal mesh 10.

TABLE 1

| Atomic Concentration (atom %) | C | Ni |
|---|---|---|
| Before Cleaning | 84 | (detection limit or less) |
| After Cleaning | 22 | 27 |

According to Table 1, a large amount of carbon (C) was detected before cleaning. After completion of cleaning, the amount of carbon was significantly lower than that before cleaning and the concentration of carbon was lower than that of nickel (Ni), which is a main component of the metal mesh 10. In other words, when XPS shows that the concentration of carbon is lower than that of metal (nickel) on the surface of the metal mesh 10, it can be determined that cleaning has been completed.

As described above, by attaching the organic material 20 to the metal mesh 10 it is possible to determine whether the metal mesh 10 has been sterilized and cleaned on the basis of the relative conditions of the organic material 20 before and after the sterilization step and the cleaning step.

The following advantageous effects can be obtained using the foregoing embodiment.

In the metal mesh 10, the organic material 20 for determining whether sterilization and cleaning have been completed is attached to both the first principal surface PS1 and the inside of the through-holes 11. This configuration makes it easy to determine whether sterilization and cleaning have been completed on the basis of the conditions of the organic material 20 before and after the sterilizing and cleaning steps for the metal mesh 10.

A photosensitive organic material, specifically, a radiation-sensitive organic material that undergoes a modification by radiation exposure is preferably used as the organic material 20. For example, when sterilization is performed by gamma-ray exposure, the organic material 20 undergoes a modification by gamma-ray exposure. This makes it easy to determine whether the metal mesh 10 has been sterilized on the basis of the modification of the organic material 20 by gamma-ray exposure.

The sterilization determination method preferably focuses on a change in color attributed to the modification of the organic material 20 by gamma-ray exposure. In this method, whether the metal mesh 10 has been sterilized is determined on the basis of the absorbance of the organic material 20 before and after the sterilizing step. In the preferred sterilization determination method, a change in the color of the organic material 20 can be thus detected by measuring the absorbance of the organic material 20, which makes it easy to determine whether the metal mesh 10 has been sterilized.

The organic material 20 preferably contains carbon. In the cleaning determination method, whether the metal mesh 10 has been cleaned can be easily determined by measuring the amount of carbon in the organic material 20 before and after the cleaning step.

The organic material 20 is preferably easily removable from the metal mesh 10. Thus, the organic material 20 can be easily removed from the metal mesh 10 before the metal mesh 10 is used in filtering out a filtration object. As a result, the metal mesh 10 can be easily used in a filtration application, which is the intended application. In other words, the organic material 20 preferably does not hinder filtration when the metal mesh 10 is used for filtration.

In the first embodiment, the organic material 20 is attached to part of the area of the metal mesh 10 which has through-holes 11 on the first principal surface PS1. However, the organic material 20 is not necessarily attached to this area. The organic material 20 is attached to at least part of the metal mesh 10. For example, the organic material 20 may be attached to part of the first principal surface PS1, part of the second principal surface PS2, part of the inner walls of the through-holes 11, or other parts of the metal mesh 10. The organic material 20 may be attached to the entire first principal surface PS1. When the organic material 20 is attached to the entire first principal surface PS1, areas in which the organic material 20 is not modified in the sterilizing step can be specified. That is, areas in which sterilization is not done well can be specified. Similarly, areas in which cleaning is not done well in the cleaning step can also be specified by measuring the amount of carbon in the organic material 20.

In the first embodiment, an example in which the organic material 20 is an organic material for determining whether sterilization and cleaning have been completed is described. However, the organic material 20 is not limited to this organic material. The organic material 20 may be an organic material for determining whether at least one of sterilization and cleaning has been completed. For example, to determine only whether sterilization has been completed, the organic material 20 does not need to contain carbon and may be a radiation-sensitive organic material that undergoes a modification by radiation exposure. To determine only whether cleaning has been completed, the organic material 20 contains carbon does not need to undergo a modification by radiation exposure.

In the first embodiment, an example in which the organic material 20 is a radiation-sensitive organic material that undergoes a modification by gamma-ray exposure is described. However, the organic material 20 is not limited to this organic material. The organic material 20 may be changed according to the type of sterilization process. When, for example, ultraviolet rays are used, the organic material 20 may be a photosensitive organic material that undergoes a modification by ultraviolet rays. When ozone is used, the organic material 20 may be an organic material that undergoes a modification (oxidation) by ozone. In Step ST13 of determining whether sterilization has been completed, whether sterilization has been completed may be determined by reculture typified by bacterial culture in an agar medium. However, the determining process is not limited to this. For example, whether sterilization has been completed may be determined by Gram staining or the like.

In the first embodiment, an example in which the modification of the organic material 20 refers to a change in the color of the organic material 20 in response to gamma-ray exposure has been described. However, the modification is not limited to a change in the color. For example, the modification may be a change in the composition of the organic material 20, a change in viscosity, a change in hardness, or the like.

In the first embodiment, an example in which the sterilizing step ST12 involves sterilization by gamma-ray exposure has been described. However, the sterilizing step ST12 is not limited to this. Examples of the sterilizing step ST12 include autoclave sterilization by high-temperature, high-pressure saturated steam, ethylene oxide gas sterilization using ethylene oxide gas, and oxidation sterilization by ozone.

In the first embodiment, the organic material 20 contains carbon in order to easily determine whether the cleaning step has been completed. However, the organic material 20 may be free of carbon. For example, when completion of the cleaning step is determined on the basis of, for example, a change in the weight of the metal mesh 10 before and after the cleaning step, the organic material 20 may be free of carbon.

In the first embodiment, Step ST23 of determining whether cleaning has been completed involves determining whether cleaning has been completed by measuring the amount of carbon in the organic material 20. However, the determining step is not limited to this. Whether cleaning has been completed may be also determined by, for example, X-ray structure analysis, AFM (Atomic Force Microscope), visual observation, visible spectroscopy, infrared spectroscopy, ICP-MS (ICP-Mass Spectrometry) for eluents, and the measurement of a change in weight. The organic material 20 may be freely changed according to the method for determining whether cleaning has been completed in the cleaning determining step ST23. For example, the organic material 20 does not necessarily contain carbon in order to determine whether cleaning has been completed by measuring a change in the weight of the organic material 20.

In the first embodiment, the sterilization determination method may be performed by using a plurality of metal meshs 10. For example, in the attaching step ST11 in the sterilization determination method, the organic material 20 may be attached to at least one metal mesh 10 selected from a plurality of metal meshs 10. The metal mesh 10 having the organic material 20 may be subjected to the determining step ST13 after the plurality of metal meshs 10 are subjected to the sterilizing step ST12. This process makes it possible to efficiently determine whether all of the plurality of metal meshs 10 have been sterilized.

Similarly, the cleaning determination method may be performed by using a plurality of metal meshs 10. In the attaching step ST21 in the cleaning determination method, the organic material 20 may also be attached to at least one metal mesh 10 selected from a plurality of metal meshs 10. The metal mesh 10 having the organic material 20 may be subjected to the determining step ST23 after the plurality of metal meshs 10 are subjected to the cleaning step ST22. This process makes it possible to efficiently determine whether the plurality of metal meshs 10 have been cleaned.

In the sterilization determination method and the cleaning determination method in the first embodiment, the metal mesh 10 after sterilization or after cleaning was observed in 10 locations through an electron microscope (e.g., S-4800 available from Hitachi, Ltd.) at a magnification of ×5,000. When the organic material 20 is not observed, it is then determined that the metal mesh 10 has been successfully sterilized or cleaned.

(Second Embodiment)
[Overall Structure]
A metal mesh in a second embodiment according to the present invention will be described with reference to FIG. 7 and FIG. 8.

Figure 7:
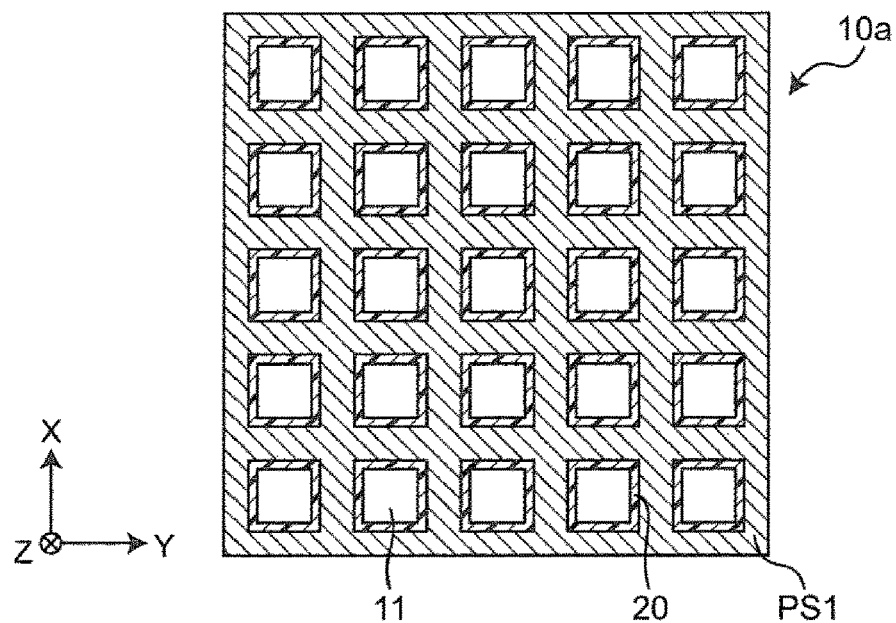
FIG. 7 is a schematic view of a part of a metal mesh in a second embodiment according to the present invention.

FIG. 7 is a schematic structural view of a metal mesh 10a in the second embodiment. FIG. 8 is an enlarged view of through-holes 11 of the metal mesh 10a.

The description of the second embodiment will focus on the differences between the first and second embodiments. In the second embodiment, elements that are the same as or similar to those in the first embodiment are provided with the same reference symbols and described. In the second embodiment, descriptions overlapping with the first embodiment are omitted.

Figure 8:
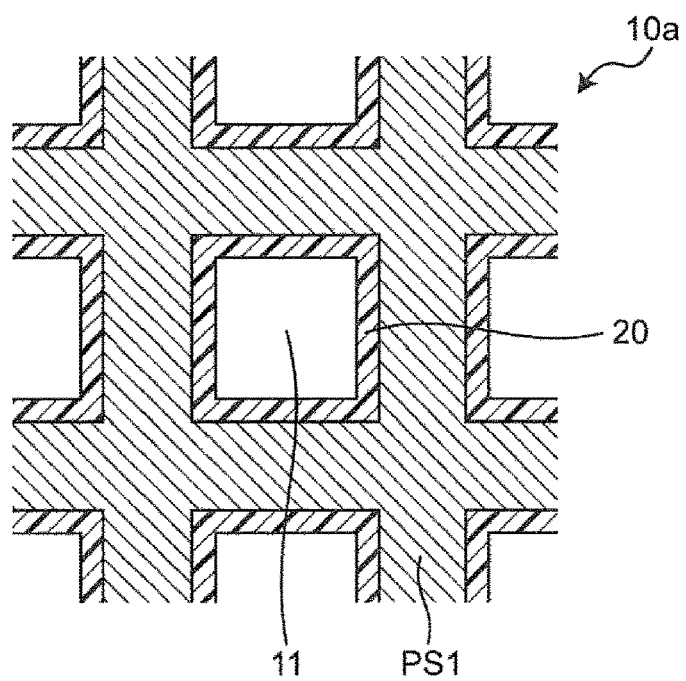
FIG. 8 is an enlarged view of through-holes in the metal mesh in the second embodiment according to the present invention.

As illustrated in FIG. 7 and FIG. 8, the metal mesh 10a in the second embodiment differs from the metal mesh 10 in the first embodiment in that an organic material 20 is attached to only the inner walls of the through-holes 11.

In the metal mesh 10a, the organic material 20 is not attached to a first principal surface PS1 or to a second principal surface of the metal mesh 10a. The organic material 20 is preferably attached to the entire inner walls of the plural through-holes 11. With this structure the following advantageous effects can be obtained.

In this embodiment, the organic material 20 is not attached to either the first or second principal surfaces PS1 or PS2. The organic material 20 is attached to the inner walls of the through-holes 11. This configuration allows the amount of the organic material 20 attached to the metal mesh 10a to be smaller than that in the first embodiment, which achieves cost reduction.

The inner walls of the through-holes 11 are locations that are difficult to expose to gamma rays in the sterilizing step, that is, locations that are difficult to sterilize. Whether the metal mesh 10a has been sterilized well can be easily determined by determining whether sterilization has been completed on the basis of a change in the color of the organic material 20 attached to the inner walls of the through-holes 11 before and after the sterilizing step. Similarly, the inner walls of the through-holes 11 are also locations that are difficult to clean in the cleaning step. Whether the metal mesh 10a has been cleaned well can also be easily determined by determining whether cleaning has been completed on the basis of the amount of carbon in the organic material 20 attached to the inner walls of the through-holes 11 before and after the cleaning step.

In the second embodiment, an example in which the organic material 20 is attached to the entire inner walls of the plural through-holes 11 is described. However, the organic material 20 is not necessarily attached to the entire inner walls. For example, the organic material 20 may be attached to part of the inner walls of the through-holes 11.

(Third Embodiment)
[Overall Structure]
A metal mesh according to a third embodiment of the present invention will be described with reference to FIG. 9.

Figure 9:
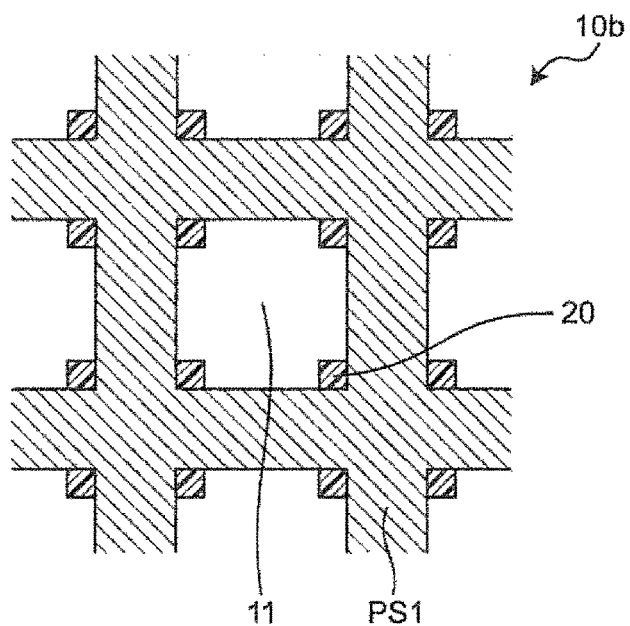
FIG. 9 is an enlarged view of through-holes in a metal mesh in a third embodiment according to the present invention.

FIG. 9 is a schematic structural view of a metal mesh 10b in the third embodiment. FIG. 9 is an enlarged view of through-holes 11 of the metal mesh 10b.

The description of the third embodiment will focus on the differences between the second and third embodiments. In the third embodiment, elements that are the same as or similar to those in the second embodiment are provided with the same reference symbols and described. In the third embodiment, descriptions overlapping with the second embodiment are omitted.

As illustrated in FIG. 9, the metal mesh 10b in the third embodiment differs from the metal mesh 10a in the second embodiment in that an organic material 20 is attached not to the entire inner walls of the through-holes 11 but to part of the inner walls of the through-holes 11. More particularly, the organic material 20 is attached to the corners of the inner walls of the through-holes 11.

According to the metal mesh 10b in the third embodiment, the following advantageous effects can be obtained.

In the metal mesh 10b, the organic material 20 is attached to the corners of the inner walls of the through-holes 11. The corners of the inner walls of the through-holes 11 are locations that are most difficult to expose to gamma rays in the sterilizing step, that is, locations that are most difficult to sterilize. Thus, whether the metal mesh 10b has been sterilized well can be easily determined by attaching the organic material 20 to the corners of the inner walls of the through-holes 11. Similarly, the corners of the inner walls of the through-holes 11 are also locations that are most difficult to clean in the cleaning step. Thus, whether the metal mesh 10b has been cleaned well can also be easily determined.

The amount of the organic material 20 attached to the metal mesh 10b is less than that in the second embodiment, which achieves further cost reduction.

In the third embodiment, an example in which the organic material 20 is attached to the corners of the inner walls of the through-holes 11 is described. However, the organic material 20 is not necessarily attached to the corners of the inner walls. The organic material 20 may be attached to at least part of the inner walls of the through-holes 11. For example, the organic material 20 may be attached to at least one of four corners of the inner walls of the through-holes 11. The organic material 20 may be attached to at least part of the inner walls of the through-holes 11 in the thickness direction of the metal mesh 10.

Hereinafter, Examples of the present invention will be described.

EXAMPLE 1

Two metal meshes were subject to the same sterilization process, one having an organic material attached to its surface and one not.

Example 1 was a metal mesh 10 made of nickel and having white polyacetal, which is an organic material 20, attached to part of its surface. Comparative Example 1, used to compare with Example 1, was a metal mesh 10 made of nickel and having no organic material 20.

Example 1 and Comparative Example 1 were collectively provided as the same lot and sterilized by gamma-ray exposure. The beam source was cobalt 60 and the beam dose was 28.2 to 29.4 kGy. It was determined that the white polyacetal turned yellow in Example 1 making it easy to visually determine that all metal meshes in this lot had been sterilized in Example 1. No difference in Comparative Example 1 between before and after the sterilizing step was visually observed. That is, it was not possible to determine whether Comparative Example 1 had been sterilized.

Figure 10:
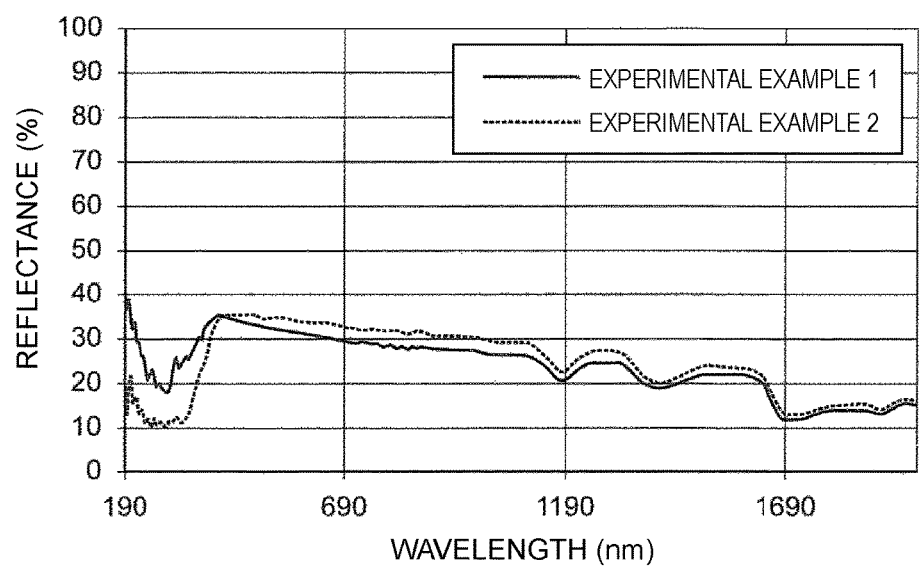
FIG. 10 is a graph showing the results of absorption spectrometry of Example 1 before gamma-ray exposure and after gamma-ray exposure.

FIG. 10 illustrates the results of absorption spectrometry of polyacetal in Example 1 before gamma-ray exposure and after gamma-ray exposure by using an ultraviolet-visible absorptiometer (Model U-4100 available from Hitachi High-Technologies Corporation). An integrating sphere was used in detection and the total reflectance of the polyacetal surface for light ranging from ultraviolet light to near-infrared light was calculated. In FIG. 10, the horizontal axis represents wavelength (nm) and the vertical axis represents reflectance (%). In FIG. 10, Experimental Example 1 corresponds to the result of absorption spectrometry of Example 1 before gamma-ray exposure, and Experimental Example 2 corresponds to the result of absorption spectrometry of Example 1 after gamma-ray exposure.

FIG. 10 indicates that the reflectance of Experimental Example 2 is lower than that of Experimental Example 1 in a wavelength range from 200 nm to 400 nm because of gamma-ray exposure. In other words, the absorption of light by Experimental Example 2 in a wavelength range from 200 nm to 400 nm is larger, which suggests polyacetal turned yellow.

EXAMPLE 2

In Example 2, an organic material 20 was applied directly on an entire first principal surface PS1 of a metal mesh 10 made of nickel. The organic material 20 contains a quinonediazide compound and a novolac resin. The quinonediazide compound is a photosensitive organic material and serves as a photosensitizer.

A method for producing Example 2 will be described. The organic material 20 in a liquid form was applied to the first principal surface PS1 of the metal mesh 10 using a spin coater by dropping 5 ml of the organic material 20 onto the first principal surface PS1. The rotation speed of the spin coater was 1500 rpm (this rotation speed was reached in a second) and the rotation time was 1 minute. As a result, the organic material 20 was attached to both the first principal surface PS1 and the inside the through-holes 11. The film thickness of the organic material 20 on the first principal surface PS1 was 2 µm. Example 2 and Comparative Example 1 were collectively provided as the same lot and sterilized by gamma-ray exposure. As a result, the organic material 20, which was brown, slightly turned black in Example 2. This made it easy to visually determine that all metal meshes in this lot had been sterilized.

Subsequently, Example 2 was subjected to ultrasonic cleaning (frequency 45 kHz) with acetone for 10 minutes. After cleaning, a nickel color was visually observed on the first principal surface PS1. This indicates that the organic material 20 was easily removed from the metal mesh 10. Therefore, the metal mesh 10 was easily used in a filtration application, which was the intended application.

EXAMPLE 3

Example 3 had an organic material 20 located directly on only the inner walls of through-holes 11 of a metal mesh 10a. The organic material 20 contained a quinonediazide compound and and a novolac resin. The quinonediazide compound is a photosensitive organic material and serves as a photosensitizer.

Example 3 was produced as follows. A step for attaching the organic material 20 to only the inner walls of the through-holes 11 is added to the process for producing Example 2. In the production of Example 3, after the process for producing Example 2, the metal mesh 10a having the organic material 20 was heated at a set temperature of 130° C. in a nitrogen gas atmosphere for 5 minutes to volatilize part of a solvent component. The hardness of the organic material was then adjusted by exposure to a beam of light having an energy density of 2500 J/m2 and including a wavelength of 365 nm for 0.25 seconds. Finally, ultrasonic cleaning (frequency 45 kHz) with acetone was performed for 3 seconds to remove part of the organic material 20 on the first principal surface PS1 and inside the through-holes 11, so that the organic material 20 was attached to only the inner walls of the through-holes 11. The thickness of the organic material 20 attached to the inner walls of the through-holes 11 should be 0.7 µm or less. Ultrasonic cleaning (frequency 45 kHz) with acetone was performed again for 7 seconds and the organic material 20 was not observed on the inner walls of the through-holes 11.

Figure 11:
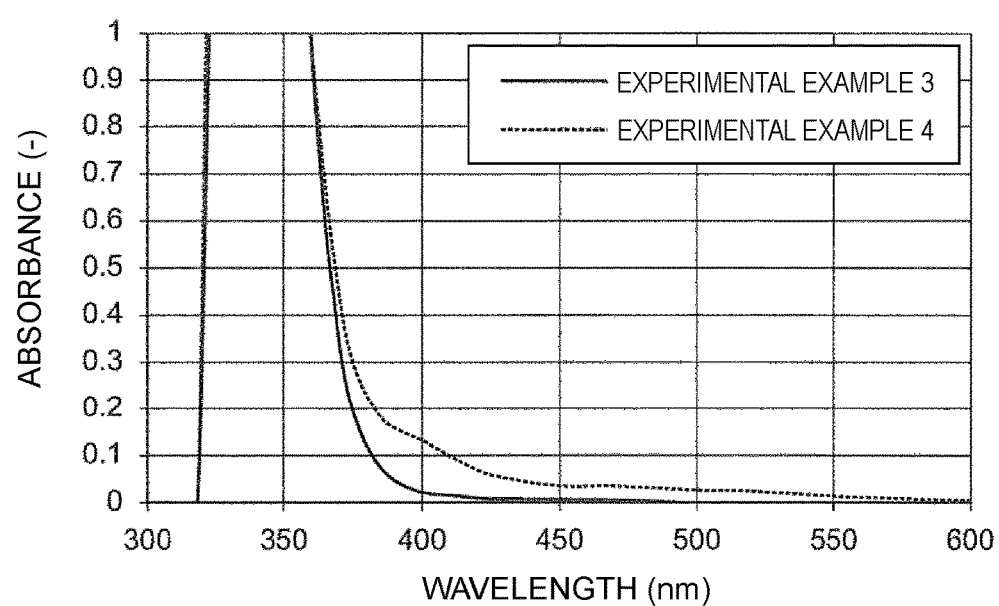
FIG. 11 is a graph showing the results of absorption spectrometry of Example 3 before gamma-ray exposure and after gamma-ray exposure.

Example 3 and Comparative Example 1 were collectively provided as the same lot and sterilized by gamma-ray exposure. Subsequently, the inner walls of the through-holes 11 of Example 3 were analyzed by microspectrophotometry. The results are shown in FIG. 11. FIG. 11 illustrates the results of absorption spectrometry of the organic material 20 in Example 3 before and after gamma-ray exposure by using an ultraviolet-visible absorptiometer (Model U-4100 available from Hitachi High-Technologies Corporation). An integrating sphere was used in detection and the absorbance of the organic material 20 in Example 3 for light ranging from ultraviolet light to near-infrared light was calculated. In FIG. 11, the horizontal axis represents wavelength (nm) and the vertical axis represents absorbance. FIG. 11 depicts only the wavelength range from 300 nm to 600 nm. Experimental Example 3 corresponds to the result of absorption spectrometry of Example 3 before gamma-ray exposure and Experimental Example 4 corresponds to the result of absorption spectrometry of Example 3 after gamma-ray exposure.

FIG. 11 reveals that the absorbance of Experimental Example 4 is higher than that of Experimental Example 3 in a wavelength range from 390 nm to 580 nm because of gamma-ray exposure. This suggests that the organic material 20 in Experimental Example 4 changed in color in response to gamma-ray exposure.

Subsequently, Example 3 was subjected to ultrasonic cleaning (frequency 45 kHz) with acetone for 5 minutes, and the inner walls of the through-holes 11 were then analyzed by microspectrophotometry. As a result, a nickel color was observed. This indicates that the organic material 20 is easily removable from the metal mesh 10a. Therefore, the metal mesh 10a was easily used in a filtration application, which was the intended application.

EXAMPLE 4

Example 4 attaches an organic material 20 to only the inner walls of through-holes 11 of the metal mesh 10a as in Example 3.

Example 4 and Comparative Example 1 were collectively provided as the same lot and sequentially subjected to vibration cleaning with acetone, ethanol, pure water, and ethanol each for 10 minutes. After cleaning, the organic material 20 was not observed on the inner walls of the through-holes 11 as a result of observation through a microscope. This shows that all metal meshs in this lot had been cleaned.

Although the present invention is fully described in connection with its preferred embodiments with reference to the accompanying drawings, various modifications and alterations will be apparent to those skilled in the art. It should be understood that these modifications and alterations are within the scope of the present invention defined by the accompanying claims unless they are out of the scope of the present invention.

The present invention is advantageous in that whether the metal mesh has been sterilized or cleaned is determined on the basis of the organic material attached to the metal mesh. The metal mesh is useful in various fields, such as chemical analysis, drug discovery and manufacture, clinical laboratory testing, public health management, and environmental measurement.

The invention claimed is:

1. A combination comprising a metal mesh having a plurality of through-holes and a photosensitive organic material attached to at least part of the metal mesh, wherein the photosensitive organic material is attached to only at least part of inner walls of the plurality of through-holes.

2. The combination according to claim 1, wherein the photosensitive organic material is a radiation-sensitive organic material that undergoes a modification in response to radiation exposure.

3. The combination according to claim 1, wherein the photosensitive organic material is a polymer compound that produces polymer radicals when exposed to radiation.

4. The combination according to claim 3, wherein the radiation is gamma-ray radiation.

5. The combination according to claim 1, wherein the through-holes have corners and the photosensitive organic material is attached only to the corners.

6. A sterilization determination method for determining whether a metal mesh has been sterilized, the method comprising:
attaching a photosensitive organic material to only at least part of inner walls of the plurality of through-holes.

7. The sterilization determination method according to claim 6, wherein the determination of whether the metal mesh has been sterilized involves measuring absorbances of the photosensitive organic material both before and after the mesh has been sterilized and determining whether the metal mesh has been sterilized on a basis of the measured absorbances.

8. The sterilization determination method according to claim 6, wherein photosensitive organic material is attached to at least one metal mesh selected from a plurality of metal meshs which are sterilized together.

9. The sterilization determination method according to claim 6, wherein the photosensitive organic material is a radiation-sensitive organic material that undergoes a modification in response to radiation exposure.

10. The sterilization determination method according to claim 6, wherein the photosensitive organic material is a polymer compound that produces polymer radicals when exposed to radiation.

11. The sterilization determination method according to claim 10, wherein the radiation is gamma-ray radiation.

12. The sterilization determination method according to claim 6, wherein the through-holes have corners and the photosensitive organic material is attached only to the corners.

13. A cleaning determination method for determining whether a metal mesh has been cleaned, the method comprising:
attaching a photosensitive organic material to at least part of the metal mesh;
cleaning the metal mesh; and
determining whether the metal mesh has been cleaned on a basis of an amount of the photosensitive organic material attached to the metal mesh.

14. The cleaning determination method according to claim 13, wherein the determination of whether the metal mesh has been cleaned involves measuring amounts of carbon in the photosensitive organic material both before and after the metal mesh has been cleaned and determining whether the metal mesh has been cleaned on a basis of the measured amounts of carbon.

15. The cleaning determination method according to claim 13, wherein the photosensitive organic material is attached to at least one metal mesh selected from a plurality of metal meshs which are cleaned together.

* * * * *